United States Patent
Biedermann et al.

(10) Patent No.: US 8,613,768 B2
(45) Date of Patent: *Dec. 24, 2013

(54) SPACE KEEPER FOR VERTEBRAE OR INTERVERTEBRAL DISKS

(75) Inventors: Lutz Biedermann, VS-Villingen (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/860,671

(22) Filed: Aug. 20, 2010

(65) Prior Publication Data

US 2011/0040385 A1 Feb. 17, 2011

Related U.S. Application Data

(63) Continuation of application No. 10/660,453, filed on Sep. 11, 2003, now Pat. No. 7,828,846.

(30) Foreign Application Priority Data

Sep. 12, 2002 (DE) .................................. 102 42 331

(51) Int. Cl.
A61F 2/44 (2006.01)
(52) U.S. Cl.
USPC ..................................... 623/17.14; 623/17.15
(58) Field of Classification Search
USPC ........................ 623/17.11, FOR. 17
See application file for complete search history.

(56) References Cited

U.S. PATENT DOCUMENTS

| 4,759,766 A | 7/1988 | Buettner-Janz et al. |
| 4,820,305 A | 4/1989 | Harms |
| 4,932,975 A | 6/1990 | Main et al. |
| 5,071,437 A | 12/1991 | Steffee |
| 5,314,477 A | 5/1994 | Marnay |
| 5,370,697 A | 12/1994 | Baumgartner |
| 5,375,823 A | 12/1994 | Navas |
| 5,401,269 A | 3/1995 | Buttner-Janz et al. |
| 5,480,442 A | 1/1996 | Bertagnoli |
| 5,507,816 A | 4/1996 | Bullivant |
| 5,534,029 A | 7/1996 | Shima |
| 5,540,688 A | 7/1996 | Navas |
| 5,609,637 A | 3/1997 | Biedermann et al. |

(Continued)

FOREIGN PATENT DOCUMENTS

| CN | 1106248 A | * 8/1995 | ................ A61F 2/28 |
| DE | 2 263 842 A | 7/1974 | |

(Continued)

OTHER PUBLICATIONS

English translation of JP 49-11836 (Mar. 19, 1974).*

(Continued)

*Primary Examiner* — David H Willse
(74) *Attorney, Agent, or Firm* — Christie, Parker & Hale, LLP

(57) ABSTRACT

A space keeper for vertebrae or intervertebral disks is provided, which has a tubular section and teeth on the respective ends of the space keeper. On at least one end of the tubular section an element is provided, which has a top plate which is tiltable about an angle to the longitudinal axis of the tubular section.

25 Claims, 3 Drawing Sheets

(56) References Cited

U.S. PATENT DOCUMENTS

| | | |
|---|---|---|
| 5,676,701 A | 10/1997 | Yuan et al. |
| 5,702,451 A | 12/1997 | Biedermann et al. |
| 5,776,198 A | 7/1998 | Rabbe et al. |
| 5,827,328 A | 10/1998 | Buttermann |
| 5,989,290 A | 11/1999 | Biedermann et al. |
| 6,375,682 B1 | 4/2002 | Fleischmann et al. |
| 6,527,804 B1 | 3/2003 | Gauchet et al. |
| 6,682,562 B2 | 1/2004 | Viart et al. |
| 6,764,512 B2 | 7/2004 | Keller |
| 6,936,071 B1 | 8/2005 | Marnay et al. |
| 7,037,340 B2 | 5/2006 | Gau |
| 7,066,958 B2 | 6/2006 | Ferree |
| 7,235,102 B2 | 6/2007 | Ferree et al. |
| 2001/0016773 A1 | 8/2001 | Serhan et al. |
| 2002/0128715 A1 | 9/2002 | Bryan et al. |
| 2002/0156528 A1 | 10/2002 | Gau |
| 2003/0045939 A1 | 3/2003 | Casutt |
| 2003/0191534 A1 | 10/2003 | Viart et al. |
| 2004/0024460 A1 | 2/2004 | Ferree |
| 2004/0117021 A1 | 6/2004 | Biedermann et al. |
| 2004/0153157 A1 | 8/2004 | Keller |
| 2005/0085917 A1 | 4/2005 | Marnay et al. |
| 2005/0251260 A1 | 11/2005 | Gerber et al. |
| 2005/0267581 A1 | 12/2005 | Marnay et al. |

FOREIGN PATENT DOCUMENTS

| | | |
|---|---|---|
| DE | 28 04 936 A1 | 8/1979 |
| DE | 30 23 353 C2 | 4/1982 |
| DE | 3529 761 A1 | 8/1985 |
| DE | 39 11 610 A1 | 10/1990 |
| DE | 42 13 771 C1 | 4/1992 |
| DE | 41 09 941 A1 | 10/1992 |
| DE | 42 08 116 A1 | 9/1993 |
| DE | 43 23 034 C1 | 7/1994 |
| DE | 42 08 116 C2 | 8/1995 |
| DE | 299 11 422 U1 | 8/1999 |
| DE | 239 523 A1 | 7/2005 |
| EP | 0 176 728 A1 | 4/1986 |
| EP | 0 268 115 B1 | 10/1987 |
| EP | 0 356 112 A1 | 2/1990 |
| EP | 0 392 076 A1 | 10/1990 |
| EP | 0 630 625 A2 | 12/1994 |
| EP | 0 747 025 A1 | 12/1996 |
| EP | 0 955 021 A1 | 11/1999 |
| EP | 1 346 709 A2 | 9/2003 |
| JP | 49-11836 | 3/1974 |
| JP | 2001-246592 A * | 9/2001 ............... A61F 2/30 |
| JP | 2001-526083 | 12/2001 |
| WO | WO 93/10725 | 6/1993 |
| WO | WO 95/26697 A1 | 10/1995 |
| WO | WO 99/32055 | 7/1999 |
| WO | WO 00/35384 A1 | 6/2000 |
| WO | WO 01/08612 A1 | 2/2001 |
| WO | WO 01/68003 A1 | 6/2001 |
| WO | WO 01/68003 A1 | 9/2001 |
| WO | WO 02/11650 A2 | 2/2002 |
| WO | WO 02/47586 A1 | 6/2002 |
| WO | WO 03/094806 A1 | 11/2003 |
| WO | WO 2004/016217 A2 | 2/2004 |

OTHER PUBLICATIONS

English-language version of Aug. 26, 2008 Office action from the Japan Patent Office for counterpart foreign application 318697/2003 discussing JP 49-11836, 3 sheets.

U.S. Appl. No. 60/379,462, filed May 10, 2002.

Euopean Search Report for Application No. 03017383.5-2310 dated Jan. 8, 2004.

European Search Report for Application No. 03017959.2 dated Jan. 29, 2004.

European Search Report for Application No. 03017959.2-2310 dated Oct. 21, 2003.

* cited by examiner

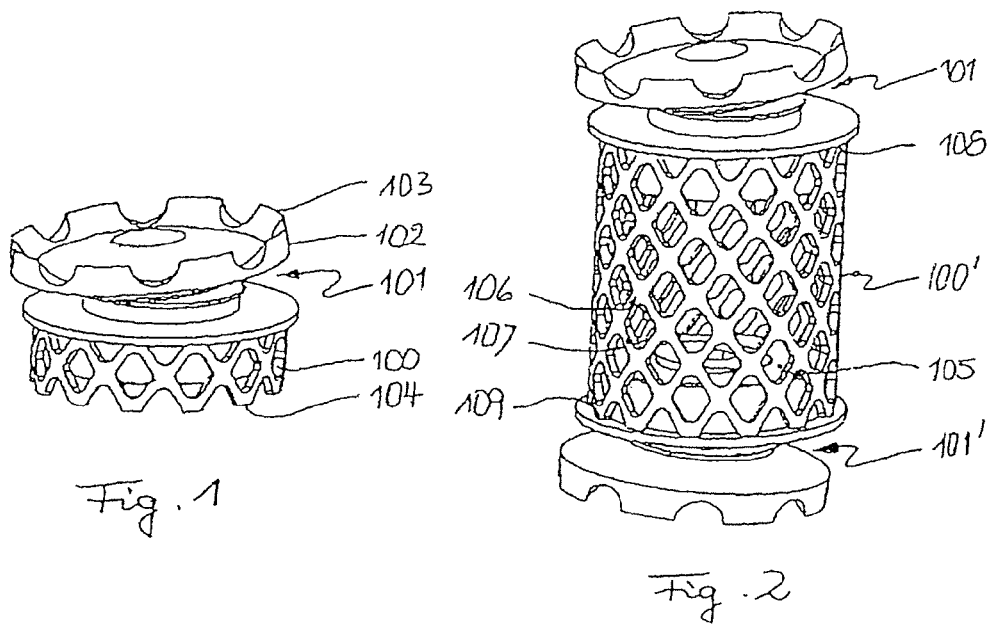
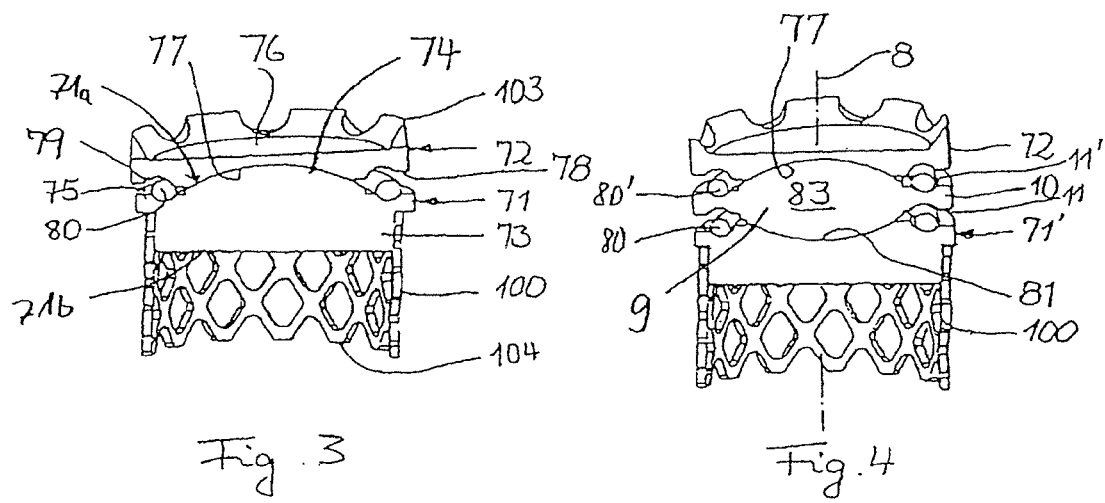

SPACE KEEPER FOR VERTEBRAE OR INTERVERTEBRAL DISKS

CROSS-REFERENCE TO RELATED APPLICATION(S)

This application is a continuation of application Ser. No. 10/660,453 filed Sep. 11, 2003, now U.S. Pat. No. 7,828,846, which claims priority to and the benefit of German Patent Application No. 102 42 331.8 filed on Sep. 12, 2002, the disclosures of which are fully incorporated herein by reference.

BACKGROUND

The invention relates to a space keeper for vertebrae or intervertebral disks. Space keepers for replacing a vertebra such as that disclosed in EP 0 268 115 B are known in the prior art. This prior art space keeper is a cylindrically shaped element having open ends that engage the adjacent vertebrae, so that fusion takes place between the two adjoining vertebrae and the intervening space keeper.

A prior art space keeper for replacing a removed intervertebral disk is also disclosed in DE 43 23 034. This space keeper is inserted between two adjacent vertebrae as a replacement for a removed intervertebral disk. The space keeper engages with its open ends the walls of the adjacent vertebrae so that fusion takes place between the two adjoining vertebrae.

BRIEF SUMMARY

An object of the present invention is to create a space keeper for both vertebrae and intervertebral disks which has the properties of the space keeper described in the prior art and which allows for a movable connection between the space keeper and the adjoining vertebral body.

In one embodiment, the space keeper for vertebrae or intervertebral disks comprises a tubular section having a longitudinal axis, a base plate connected with an end of the tubular section and a top plate connected with the base plate. In this embodiment, the top plate is tiltable about an angle to the longitudinal axis of the tubular section.

In another embodiment, the space keeper for vertebrae or intervertebral disks comprises a tubular section having a longitudinal axis and a first end and a second end. The space keeper further comprises a first element proximate to the first end of the tubular section wherein the first element has a base plate connected with the first end of the tubular section. The first element also has a top plate connected with the base plate and an elastic member located between the top plate and the base plate. The space keeper further comprises a second element proximate to the second end of the tubular section wherein the second element has a base plate connected with the second end of the tubular section. The second element also has a top plate connected with the base plate and an elastic member located between the top plate and the base plate. In this embodiment, the top plates are tiltable about an angle to the longitudinal axis of the tubular section.

Advantages of the present invention will become readily apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 1 is a perspective side view of a space keeper with a movable element on one side according to a preferred embodiment of the present invention;

FIG. 2 is a perspective side view of a space keeper with movable elements on each end according to a preferred embodiment of the present invention;

FIG. 3 is a sectional view of a space keeper according to a preferred embodiment of the present invention;

FIG. 4 is a sectional view of a space keeper according to a preferred embodiment of the present invention;

DETAILED DESCRIPTION OF THE DRAWINGS AND THE PRESENTLY PREFERRED EMBODIMENTS

Figure 5:
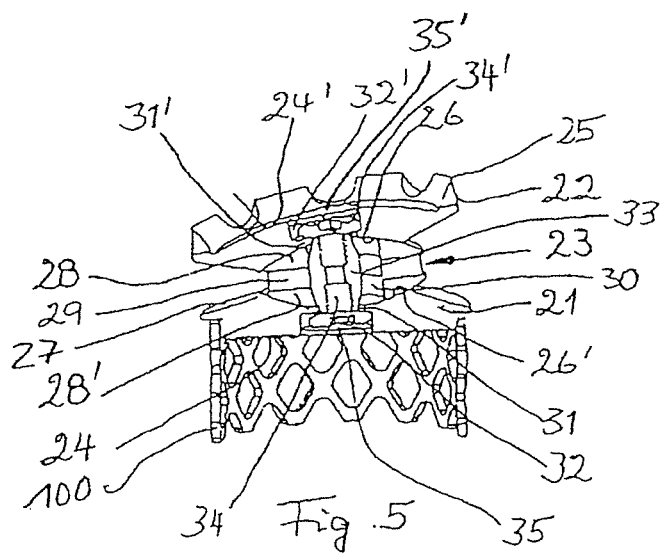
FIG. 5 is a sectional view of a space keeper according to a preferred embodiment of the present invention.

FIG. 1 shows a first preferred embodiment of a spacer keeper. The spacer keeper comprises a tubular section 100 whose length is relatively short in relation to its diameter. The spacer keeper further comprises an element 101 that is connected with an end of the tubular section 100. The element 101 has a top plate 102 that, as will be described in more detail below, is constructed to be movable relative to the tubular section 100. Both the top plate 102 and the tubular section 100 have teeth 103, 104, respectively, for engaging the adjacent vertebral body end faces. A space keeper having a relatively short tubular section is intended in particular for replacing a removed intervertebral disk.

FIG. 2 shows another preferred embodiment of the space keeper. The space keeper of FIG. 2 is similar to that of FIG. 1, however, unlike the relatively short tubular section 100 of the embodiment in FIG. 1, the tubular section 100' of the embodiment in FIG. 2 is relatively longer. Also, unlike the open end of the tubular section 100 of the embodiment of FIG. 1, the tubular section 100' of the embodiment of FIG. 2 is connected with a second element 101' having a second top plate at the end opposite that of the first element 101 and top plate. An upper edge 108 and a lower edge 109 of the tubular section 100' extend in a plane perpendicular to the longitudinal axis of the tubular section 100'. Construction of the two elements 101 and 101' is preferably identical. Because of the relatively longer length of the tubular section 100', this embodiment serves in particular as a replacement for one or more vertebrae.

FIGS. 1 and 2 show a preferred embodiment of the structure of the tubular sections 100, 100'. As can be seen in FIGS. 1 and 2, the tubular sections 100, 100' have recesses 105 that promote growing in of the bone material. The shape and pattern of the recesses is, for example, described in U.S. Pat.

Nos. 4,820,305 and 5,702,451 which are incorporated herein by reference. The tubular sections 100, 100' are generally cylindrical casings having lozenge-shaped recesses 105. The lozenge-shaped recesses 105 extend with their longitudinal diagonals parallel to the longitudinal axis of the casing. Respectively adjacent rows of these lozenge-shaped recesses 105 are staggered by half the height of a lozenge in the direction of the longitudinal axis of the casing. As a result, a network of flat strips 106, 107 are formed, intersecting one another at acute angles and are angled at respectively equal-sized angles towards the longitudinal diagonal of the lozenge-shaped recesses 105.

Hereinafter, various preferred embodiments of the elements comprising a space keeper using the above described tubular sections are described in FIGS. 3 to 11.

As can be seen from the figures, each embodiment of the space keeper has a base plate and a top plate. In the preferred embodiment of the space keeper shown in FIG. 3, the space keeper comprises a base plate 71 and a top plate 72. The base plate 71 is generally cylindrical and comprises a side 71a that faces the top plate 72 and a side 71b that faces away from the top plate 72. The side facing the top plate 72 has a face with a flat edge 75, the diameter of which face is identical to the diameter of the top plate 72. The flat edge 75 of the base plate 71 has a first annular recess 79 having an arc-like cross-section. A cylindrical section 73 is connected with the side of the base plate 71 facing away from the top plate 72. An end of the tubular section 100 is placed on to the cylindrical section 73 to form a snug fit. The diameter of the cylindrical section 73 is preferably slightly smaller, preferably 5% to 10% smaller, than the diameter of the base plate 71 so that the base plate 71 acts as a stop to the end of the tubular section 100. An open end of the tubular section 100 comprises teeth 104 which can be brought into engagement with the adjacent vertebral body. According to a preferred embodiment, the tubular section further comprises the above-described recesses 105, which considerably promote the ability to grow in of bone material.

Still with reference to FIG. 3, the base plate 71 has on its side facing the top plate 72 a centrally arranged convex contact face 74, which is preferably spherical. This convex contact face 74 is surrounded by the flat edge 75.

The top plate 72 has an outer face 76 which is preferably flat and has on its outer edge teeth 103 extending outwards vertically relative to the outer face 76. The outer edge teeth 103 serve to engage an adjacent wall of a vertebral body end plate. The top plate further comprises a concave recess 77 on an inner face opposite the outer face 76. The concave recess is constructed so as to be congruent with the convex contact face 74. Encircling the concave recess 77 is an edge zone 78 that is parallel to the outer face 76. As can further be seen from FIG. 3, the edge zone 78 has on the side facing the base plate and adjacent to the concave recess 77 a second annular recess 79. In the embodiment shown, the annular recess 79 has an arc-like cross-section. The second annular recess corresponds with the first annular recess. A ring 80 is located between the annular recesses.

In the embodiment of the space keeper shown in FIG. 4, the top plate 72 is the same as the top plate 72 of the embodiment shown in FIG. 3. The base plate 71' differs from the previously described base plate 71, however, in that instead of the convex contact face 74, the base plate 71' comprises a concave contact face 81. The curve of the concave contact face 81 is preferably of the same dimensions as the corresponding curve of the concave recess 77 of the top plate 72. In all other features the base plate 71' and the tubular section 100 coincide with the previously described embodiments.

In this embodiment, however, a core 83 is located between the base plate 71' and the top plate 72. The core 83 has a central part 9, arranged symmetrical to the symmetrical axis 8, and generally having the shape of a biconvex lens. The outer convex faces of the central part 9 preferably have the same dimensions as the curves of faces 74 and 77 to allow the faces to cooperate therewith. The outer convex face facing the top plate defines a top convex face and the outer convex face facing the base plate defines a base convex face.

As the FIG. 4 further shows, the core 83 also has an edge zone 10, the outer diameter of which is identical to the diameter of the base plate 71' and top plate 72. The edge zone is preferably constructed such that the two faces facing the base plate 71' and the top plate 72 are constructed as parallel to one another and to the symmetrical plane of the core 83. The edge zone 10 also has on both sides annular recesses 11, 11' wherein the top annular recess 11' faces the top plate 72 and the base annular recess 11 faces the base plate 71'. The annular recesses 11, 11' have the same arc-like cross-section as the annular recesses of the base plate 71' and the top plate 72. Rings 80, 80' are arranged in annular recesses between base plate 71' and the core 9 and between the core 9 and the top plate 72, respectively.

In the above-described embodiments the base plate and the top plate are preferably made of a biocompatible material, in particular steel or titanium, for example, stainless steel 316L or a cobalt chrome alloy or titanium implant grade. The core in the embodiment shown in FIG. 4 is preferably formed from a body-compatible high-molecular polyethylene synthetic material or any other suitable biocompatible polymer or other biocompatible material. Preferably, the core is made of a high molecular weight polyethylene of the UHMWPE type with a molecular weight preferably between $2 \times 10^6$ to $10 \times 10^6$. The two rings 80, 80' are preferably formed from a body-compatible elastic synthetic material, for example medical grade silicon.

In another preferred embodiment of the space keeper shown in FIG. 5, the space keeper comprises a base plate 21, a top plate 22 and a core 23 between the base plate 21 and top plate 22.

The base plate 21 has on its surface facing the core 23 a concave contact face 26' that is symmetrical to the symmetrical axis 8. The base plate further has a first edge zone 27. In contrast to the flat edge zone 10 of the embodiment of FIG. 4, the first edge zone 27 of FIG. 5 tapers off in the shape of a truncated cone towards the outer side of the base plate 21.

The side of the base plate 21 facing away from the core 23 and the connection to the tubular section 100 are constructed in exactly the same way as in the previously described embodiments.

The top plate 22 again has teeth 25 projecting outwards. The outer face 24', as can best be seen from FIG. 5, is constructed as an arc-like convex surface, wherein the curve of the surface is chosen in such a way that it substantially corresponds to a typical concave curve of a vertebral body end plate face to be brought into contact therewith.

The side of the top plate 22 facing the core 23 is constructed in exactly the same way as the side of the base plate 21 facing the core wherein the top plate defines a concave recess 26.

The core 23 is constructed in three parts and comprises two plan-convex lenticular bodies 28, 28' that face one another with their plan faces and between which a plan-parallel plate 29 is arranged. The plan-convex lenticular body proximate to the top plate is the top plan-convex lenticular body 28 and the plan-convex lenticular body proximate to the base plate is the base plan-convex lenticular body 28'. The convex face of the top plan-convex lenticular body defines a top convex face and the convex face of the base plan-convex lenticular body defines a base convex face. The lenticular bodies 28, 28' and the plate 29 have substantially the same cross-section in diameter. The curve of the convex faces of the lenticular bodies 28, 28' corresponds to the curve of the concave recess 26 and concave contact face 26' to allow the faces to engage each other.

As can best be seen from FIG. 5, the core 23 has a bore 30, extending perpendicular to its symmetrical plane and going through its central point. At corresponding locations, the base plate 21 and the top plate 22 have continuous recesses 31, 31', extending along their symmetrical axes. On the respective sides facing the outer faces 24, 24', the continuous recesses 31, 31' are extended in diameter by countersunk bores 32, 32'. A connecting sleeve 33 is provided within the bore 30. The diameter of the connecting sleeve 33 is smaller than the diameter of the bore 30. The length of the connecting sleeve 33 is greater than the length of the bore 30 so that the connecting sleeve 33 projects with its respective end in the recess of the adjacent plate. As can be seen from FIG. 5, the ends of the connecting sleeve 33 are preferably tapered.

With respect to the base plate 21 and top plate 22, screws 34, 34' are guided through the recesses 31, 31' respectively. The screws 34, 34' are screwed into the connecting sleeve 33, wherein the heads of the screws always rest within their respective countersunk bores 32, 32'. The countersunk bores 32, 32' are slightly larger than the respective heads. The screws are tightened to such an extent that the base plate 21, top plate 22 and core 23 are connected to one another in such a way that the adjacent faces are held without play, but rotatably movable in respect of one another.

As can be seen from FIG. 5, the depth of each countersunk bores 32, 32' is slightly greater than the thickness of the heads of each screw 34, 34'. The countersunk bores 32, 32' are covered at their outer ends by cover plates 35, 35'. The difference between the depth of the countersunk bores 32, 32' and the thickness of the heads of the screws 34, 34' is designed so that the heads do not quite come up against the cover plates 35, 35' when the intervertebral disk prosthesis is pressed together by elasticity.

Figure 6:
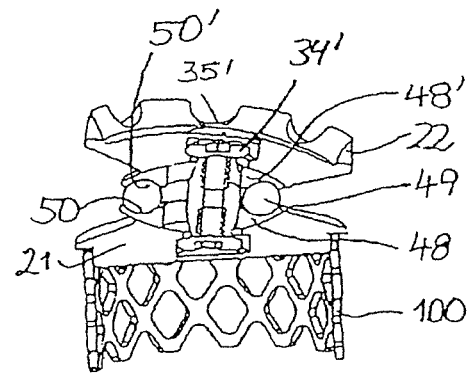
FIG. 6 is a sectional view of a space keeper according to a preferred embodiment of the present invention.

The embodiment shown in FIG. 6 differs from the embodiment shown in FIG. 5 only in the construction of the core 43. All other parts coincide with the previously described embodiment. The core 43 again has two outer plan-convex lenticular bodies 48, 48', each having convex faces that engage the base and top plates in the same way as previously described. The plan-convex lenticular body proximate to the top plate is the top plan-convex lenticular body 48' and the plan-convex lenticular body proximate to the base plate is the base plan-convex lenticular body 48. The convex face of the top plan-convex lenticular body defines a top convex face and the convex face of the base plan-convex lenticular body defines a base convex face. The central bore, connecting sleeve and the screws are also designed in the same manner as previously described. In contrast with the previous embodiment, however, instead of the plan-parallel plate 29 of the embodiment of FIG. 5, an elastic ring 49 is provided in the embodiment of FIG. 6. The faces of the lenticular bodies 48, 48' facing one another have arc-like cross-section annular recesses 50, 50'. The top plan-convex lenticular body 48' defines a first annular recess 50' and the base plan-convex lenticular body 48 defines a second annular recess 50. A ring 49 is located between the arc-like cross-section annular recesses 50, 50'.

In the embodiments shown in FIGS. 5 and 6, the connecting sleeve 33 is preferably made of a body-compatible synthetic material or of metal, for example, stainless steel 316L or titanium implant grade. The plan-parallel plate 29 and ring 49 are preferably made of a body-compatible elastic synthetic material, for example medical grade silicon or medical grade silicon rubber. The tubular section 100 is preferably formed from titanium or some other body-compatible material.

Figure 7:
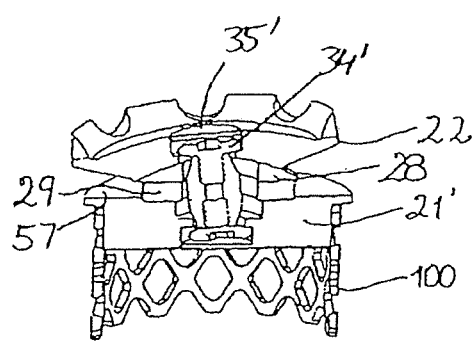
FIG. 7 is a sectional view of a space keeper according to a preferred embodiment of the present invention.

In the embodiment shown in FIG. 7, the top plate is designed in the same manner as the top plate described in FIG. 5. The base plate 21' differs from the base plate shown in FIGS. 5 and 6 only in that the surface 57 facing the top plate 22 is constructed as flat. In all other features, the base plate 21', the tubular section 100 and the top plate 22 are designed in the same manner as the embodiments described using FIGS. 5 and 6.

The space keeper of this embodiment again comprises a core 28 between the base plate 21' and the top plate 22. The core 28 has on its side facing the top plate 22 a plan-convex lenticular body 28, which is similar to the corresponding lenticular body 28 of the embodiment in FIG. 5. The face of the plan-convex lenticular body facing the top plate defines a top convex face. The space keeper of this embodiment further comprises a plan-parallel plate 29 between a flat face 57 of the base plate 21' and the plan-convex lenticular body 28. The materials of the base plate 21' and the top plate 22 and the lenticular body 28 are identical to the previously described embodiment examples. The material for plan-parallel plate 29 is the same as that for the plan-parallel plate 29 of FIG. 5.

Figure 8:
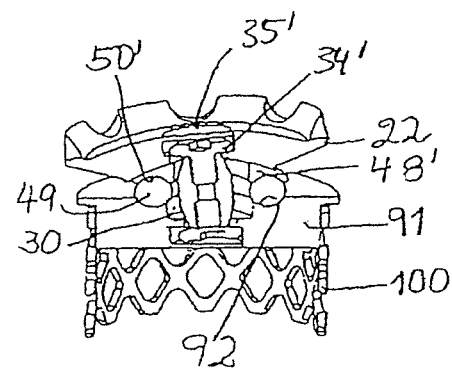
FIG. 8 is a sectional view of a space keeper according to a preferred embodiment of the present invention.

In the further preferred embodiment shown in FIG. 8, the base plate 91 differs from the base plate 21' described in FIG. 7 in that the base plate 91 has a first annular recess 92 with an arc-like cross-section directly encircling the bore 30. Instead of the core 28 of the previously described embodiment, a plan-convex lenticular body 48' is provided. The curved convex surface of the plan-convex lenticular body 48' is the top convex face which engages the concave recess of the top plate 22. The flat face of the plan-convex lenticular body 48' contains a second annular recess 50' having an arc-like cross section whose dimensions correspond to those of recess 92. A ring 49 is located between these two annular recesses.

The materials of the base plate and the top plate and the lenticular body of the core are preferably coincide with those for the previously described embodiment. The material of the ring 49 is preferably the same as that of the plan-parallel plate 29 of the previously described embodiment.

Figure 9:
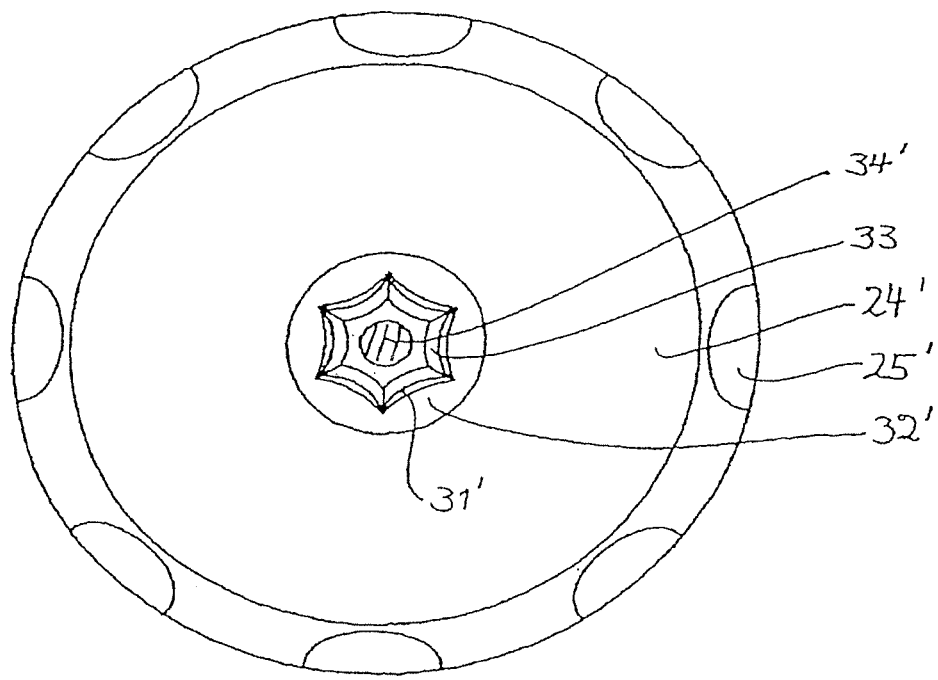
FIG. 9 is a horizontal plan view of a space keeper according to a preferred embodiment of the present invention.

FIG. 9 is a horizontal plan view of the top plate of the embodiments described in FIGS. 5 to 8, wherein the cover plate 35' and the head of the screw 34' have been omitted.

From FIG. 9 it can be seen that the connecting sleeve 33 may be hexagonal at its tapered ends. The faces between the six corners of the hexagonal section form arc-like channels. A generally hexagonal recess 31' receives the connecting sleeve 33. The faces between the six corners of the hexagonal recess 31' form arc-like curves. The diameter through two opposite corners of the recess 31' is slightly larger by a predetermined amount, preferably between 2% and 5%, than the diameter through two corresponding opposite corners of the connecting sleeve 33. The faces between the corners of the connecting sleeve 33 and recess 31' are constructed as bulging towards the center of the recess. The radius of the recess 31' curves being slightly larger by a predetermined amount, preferably between 2% and 5%, than the radius of the connecting sleeve 33 channels.

Figure 10:
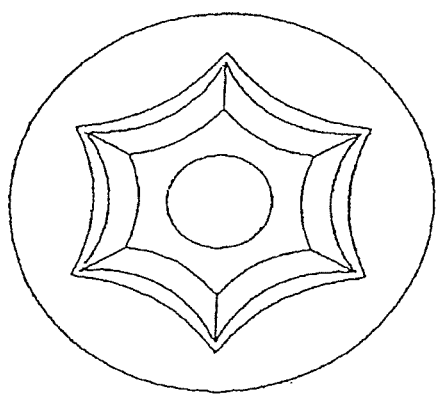
FIG. 10 is a detail from FIG. 9 on enlarged scale in a first position.
Figure 11:
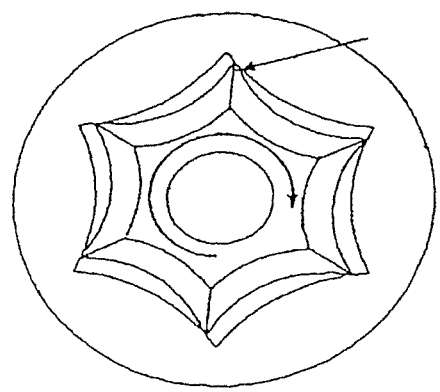
FIG. 11 is the detail shown in FIG. 10 in a second position.

As shown in FIG. 10 and FIG. 11, a rotation by a measure predetermined by the differences in size can thus take place between sleeve and top plate or sleeve and base plate. The corners of the hexagonal section of the sleeve form a mandrel abutting against the respective face of the recess 31'. In this way limitation of the rotation to a predetermined angle, preferably between 2° and 5°, is achieved.

In all the embodiments shown, the outer faces of the base and cover faces can be formed as unpolished or rough textured surface in order to achieve improvement of growing in of tissue.

In all the above-described embodiments the faces adjacent to one another and carrying out a relative movement in respect of one another can be coated with appropriate material to facilitate or improve sliding between the parts. Ceramic layers, polyethylene coatings or appropriate metal alloys, preferably polished metal alloys, are particularly suitable for this.

In the above-described embodiments adjacent and cooperating concave and convex spherical faces in various embodiments are described. The core therein has in each case the convex faces and the top plate and the base plate have associated concave spherical faces. According to a modified embodiment the face shapes can be reversed. In other words, the core can be constructed as a biconcave lenticular body or as a plan-concave lenticular body and the associated contact face of base plate and top plate is then constructed as spherically convex corresponding to the concave spherical face.

The embodiments previously described using FIGS. 3 to 8 are suitable in particular as an intervertebral disk replacement. Because the tubular section 100 is constructed like a grid, the operating surgeon can cut this tubular section to a desired length, for example to the relatively short length shown in FIG. 1. Then the space keeper thus constructed as an intervertebral disk prosthesis is inserted between two vertebrae and with the teeth engaging in the adjacent vertebral body end plates, so the plates themselves are held as fixed against rotation. The elastic rings and plates cushion the intervertebral disk prosthesis against over-severe tilting and simultaneously curb over-severe twisting about the central axis 8. The elastic rings and plates also effects shock absorption in the axial direction. In application, the outer diameter of the base and top plates is preferably slightly smaller, preferably 10% to 15% smaller, than the smallest diameter of the adjacent vertebral body end plate faces.

If the space keeper is intended for replacing one or more vertebrae, then, as shown in FIG. 2, an above-described various embodiments of top and base plates may be inserted not only from one side, but also from the other side, preferably with a snug fit, into the tubular section 100', so that the two top plates are tiltable in the above-described way about the central axis of the tubular section.

In application, after removal of the damaged vertebral body and the associated intervertebral disks, the space keeper is inserted between the remaining two vertebrae and with the teeth engaging the adjacent vertebral body end plates, so the opposite top plates are held as fixed against rotation. The function of the individual elements such as the elastic ring and plan-parallel plates takes place as described above.

The contact faces between top plate and core or base plate and core can desirably in each case be coated with materials which result in particularly good sliding pairing.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

The invention claimed is:

1. A space keeper for vertebrae or intervertebral disks comprising:

a tube having a first end, a second end, a longitudinal axis extending from the first end to the second end, and a constant cross-sectional wall thickness over the entire tube from the first end to the second end;

a base plate connected with and fixed relative to the first end of the tube, the base plate having a first section extending past the first end of the tube away from the second end of the tube, and a second section extending in a direction towards the second end of the tube and engaging the tube, wherein a longitudinal axis of the base plate is parallel to the longitudinal axis of the tube; and a top plate connected with the base plate and having a first curved surface in sliding engagement with a second curved surface of the space keeper, such that the first and second curved surfaces form complementarily curved articulating surfaces providing for rotational movement of the top plate substantially about the longitudinal axis of the base plate and sliding movement to increase or decrease an angle formed between an axis of rotation of the top plate and the longitudinal axis of the base plate.

2. The space keeper of claim 1 further comprising an elastic member located between the top plate and the base plate.

3. The space keeper of claim 2 wherein the tube defines a plurality of openings.

4. The space keeper of claim 3 wherein the openings of the tube are lozenge-shaped.

5. The space keeper of claim 3 wherein a pattern of the plurality of openings forms a grid pattern repeated along the longitudinal axis of the tube.

6. The space keeper of claim 5 wherein the pattern of the plurality of openings is continuously repeated along the longitudinal axis of the tube from the first end to the second end.

7. The space keeper of claim 6 wherein a total area of open portions in the tube exceeds a total area of wall portions.

8. The space keeper of claim 1 wherein the top plate has teeth for engaging a wall of a vertebral body end plate.

9. The space keeper of claim 8 wherein the second end of the tube has teeth configured to engage another vertebral body end plate.

10. The space keeper of claim 1, wherein the first curved surface is a concave recess on the top plate, and the second curved surface is a convex contact face on the base plate; wherein the base plate further includes a first annular recess and the top plate further includes a second annular recess; wherein the concave recess is congruent with the convex contact face; and the space keeper further comprises a ring that is located between the first annular recess and the second annular recess, wherein the ring contacts the first annular recess and second annular recess.

11. The space keeper of claim 1 wherein the first curved surface is a concave recess on the top plate, the base plate defines a concave contact face and a first annular recess; and the top plate further includes a second annular recess; and the space keeper further comprises:

a biconvex shaped core positioned between the base plate and the top plate, the core defining a base convex face and a top convex face that engage the concave contact face and concave recess, respectively, wherein the top convex face is the second curved surface, the core also defining a top annular recess and a base annular recess; and a first ring located between the first annular recess and the base annular recess and a second ring located between the top annular recess and the second annular recess.

12. The space keeper of claim 1 wherein the first curved surface is a concave recess on the top plate, the base plate defines a concave contact face; and the space keeper further comprises:
a core comprising a top plan-convex lenticular body defining a top convex face, a base plan-convex lenticular body defining a base convex face, and a plan-parallel plate between the top plan-convex lenticular body and the base plan-convex lenticular body, the core defining a bore, wherein said top convex face is the second curved surface and engages the concave recess, and said base convex face engages the concave contact face; and
a connecting sleeve located within the bore, wherein the connecting sleeve connects the top plate with the base plate.

13. The space keeper of claim 1 wherein the first curved surface is a concave recess on the top plate, the base plate defines a concave contact face; and the space keeper further comprises:
a core comprising a top plan-convex lenticular body defining a top convex face and a first annular recess, a base plan-convex lenticular body defining a base convex face and a second annular recess, wherein said top convex face is the second curved surface and engages the concave recess, and said base convex face engages the concave contact face, wherein the core also defines a bore;
a connecting sleeve located within the bore, wherein the connecting sleeve connects the top plate with the base plate; and
a ring located between the first annular recess and the second annular recess.

14. The space keeper of claim 1 wherein the first curved surface is a concave recess on the top plate, the base plate defines a flat face; and the space keeper further comprises:
a core comprising a plan-convex lenticular body defining a top convex face and a plan-parallel plate, wherein said top convex face is the second curved surface and engages the concave recess, said plan parallel plate is located between the flat face and the plan-convex lenticular body, and the core also defines a bore; and
a connecting sleeve located within the bore, wherein the connecting sleeve connects the top plate with the base plate.

15. The space keeper of claim 1 wherein the first curved surface is a concave recess on the top plate, the base plate defines a flat face having a first annular recess; and the space keeper further comprises:
a core comprising a plan-convex lenticular body defining a top convex face and a second annular recess, wherein said top convex face is the second curved surface and engages the concave recess, wherein the core also defines a bore;
a connecting sleeve located within the bore, wherein the connecting sleeve connects the top plate with the base plate; and
a ring located between the first annular recess and the second annular recess.

16. The space keeper of claim 1, further comprising:
a second base plate connected with and fixed relative to the second end of the tube, the second base plate having a first section extending past the second end of the tube away from the first end of the tube, and a second section extending in a direction towards the first end of the tube and engaging the tube, wherein a longitudinal axis of the second base plate is parallel to the longitudinal axis of the tube; and
a second top plate connected with the second base plate and having a third curved surface in sliding engagement with a fourth curved surface of the space keeper, the sliding engagement of the third and fourth curved surfaces providing for rotational movement of the second top plate substantially about the longitudinal axis of the second base plate, and sliding movement to increase or decrease an angle formed between an axis of rotation of the second top plate and the longitudinal axis of the second base plate.

17. The space keeper of claim 16 wherein the top plate and the second top plate each has teeth for engaging a wall of a corresponding vertebral body end plate.

18. The space keeper of claim 1 wherein the tube is a cylindrical casing.

19. The space keeper of claim 1 wherein the second section of the base plate extends inside a bore of the tube.

20. The space keeper of claim 19 wherein the first end of the tube abuts the first section of the base plate.

21. The space keeper of claim 1, wherein the first section of the base plate engages the first end of the tube, and wherein at the engagement, the first section of the base plate has an outer diameter that is equal to or extends radially outward from an outer diameter of the first end of the tube.

22. The space keeper of claim 1, wherein the first and second curved surfaces form curved profiles along a direction directed radially outwardly from the longitudinal, axis of the base plate.

23. A space keeper for vertebrae or intervertebral disks comprising:
a tubular section having a first end, a second end, and a longitudinal axis extending from the first end to the second end, and a coaxial bore open to the first end and the second end;
a base plate connected with and fixed relative to the first end of the tubular section, the base plate having a first section extending past the first end of the tubular section away from the second end of the tubular section, and a second section extending in a direction towards the second end of the tubular section and engaging the tubular section, wherein a longitudinal axis of the base plate is parallel to the longitudinal axis of the tubular section; and
a top plate connected with the base plate and having a first curved surface in sliding engagement with a second curved surface of the space keeper to define a spherical segment shaped contact surface with a spherical radius that is greater than a radius of the tubular section, the sliding engagement providing for rotational movement of the top plate substantially about the longitudinal axis of the base plate, and sliding movement to increase or decrease an angle formed between an axis of rotation of the top plate and the longitudinal axis of the base plate.

24. The space keeper of claim 23, wherein an entire contact surface between the first curved surface of the top plate and the second curved surface of the space keeper forms less than half of a sphere.

25. A space keeper for vertebrae or intervertebral disks comprising:
a tubular section having a first end, a second end, and a longitudinal axis extending from the first end to the second end, and a coaxial bore open to the first end and the second end;
a base plate connected with and fixed relative to the first end of the tubular section, the base plate having a first section extending past the first end of the tubular section away from the second end of the tubular section, and a second section extending in a direction towards the second end of the tubular section and engaging the tubular section, wherein a longitudinal axis of the base plate is parallel to the longitudinal axis of the tubular section; and a top plate connected with the base plate and having a first curved surface in sliding engagement with a second curved surface of the space keeper, such that the first and second curved surfaces form complementarily curved articulating surfaces providing for rotational movement of the top plate substantially about the longitudinal axis of the base plate and sliding movement to increase or decrease an angle formed between an axis of rotation of the top plate and the longitudinal axis of the base plate, wherein when a central axis of the top plate is coaxial with or otherwise parallel to the longitudinal axis of the tubular section, a portion including a largest diameter of the second curved surface is positioned closer to the first end of the tubular section than any portion of the top plate in an axial direction.

* * * * *

UNITED STATES PATENT AND TRADEMARK OFFICE
CERTIFICATE OF CORRECTION

PATENT NO. : 8,613,768 B2  Page 1 of 1
APPLICATION NO. : 12/860671
DATED : December 24, 2013
INVENTOR(S) : Lutz Biedermann et al.

It is certified that error appears in the above-identified patent and that said Letters Patent is hereby corrected as shown below:

In the Specification

Column 2, line 35      Delete "spacer"
                       Insert -- space --

Column 2, line 36      Delete "spacer"
                       Insert -- space --

Column 2, line 38      Delete "spacer"
                       Insert -- space --

Column 6, line 40      Delete "are"

In the Claims

Column 10, Claim 22, line 27      Delete "longitudinal,"
                                  Insert -- longitudinal --

Signed and Sealed this
Second Day of December, 2014

Michelle K. Lee
*Deputy Director of the United States Patent and Trademark Office*